United States Patent
Anduiza et al.

(10) Patent No.: US 6,875,231 B2
(45) Date of Patent: Apr. 5, 2005

(54) PERCUTANEOUSLY DELIVERABLE HEART VALVE

(75) Inventors: James Peter Anduiza, Costa Mesa, CA (US); Rodolfo C. Quijano, Laguna Hills, CA (US); Hosheng Tu, Newport Beach, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 9 days.

(21) Appl. No.: 10/241,718

(22) Filed: Sep. 11, 2002

(65) Prior Publication Data

US 2004/0049266 A1 Mar. 11, 2004

(51) Int. Cl.[7] .................................................. A61F 2/24
(52) U.S. Cl. ..................... 623/2.14; 623/1.15; 623/2.17; 623/2.38
(58) Field of Search ................................ 623/1.15, 1.18, 623/1.19, 1.24, 2.11–2.19, 2.38, 900, 925, 2.42

(56) References Cited

U.S. PATENT DOCUMENTS

| | | | |
|---|---|---|---|
| 5,411,552 A | | 5/1995 | Andersen et al. |
| 5,840,081 A | | 11/1998 | Andersen et al. |
| 5,957,949 A | * | 9/1999 | Leonhardt et al. ......... 623/1.24 |
| 6,168,614 B1 | | 1/2001 | Andersen et al. |
| 6,283,127 B1 | | 9/2001 | Sterman et al. |
| 6,302,907 B1 | * | 10/2001 | Hijlkema .................... 623/1.16 |
| 6,346,119 B1 | * | 2/2002 | Kuwahara et al. ......... 623/1.13 |
| 6,425,916 B1 | | 7/2002 | Garrison et al. |
| 6,440,164 B1 | * | 8/2002 | DiMatteo et al. .......... 623/1.24 |
| 6,558,418 B2 | * | 5/2003 | Carpentier et al. ........ 623/2.14 |
| 6,733,523 B2 | * | 5/2004 | Shaolian et al. ........... 623/1.35 |
| 6,733,525 B2 | * | 5/2004 | Yang et al. ................. 623/2.18 |
| 2001/0007956 A1 | | 7/2001 | Letac et al. |
| 2001/0010017 A1 | | 7/2001 | Letac et al. |
| 2002/0022875 A1 | * | 2/2002 | Strecker ..................... 623/1.15 |
| 2002/0032481 A1 | * | 3/2002 | Gabbay ...................... 623/2.11 |
| 2002/0052651 A1 | | 5/2002 | Myers et al. |
| 2002/0188344 A1 | * | 12/2002 | Bolea et al. ................ 623/1.11 |
| 2004/0049262 A1 | * | 3/2004 | Obermiller et al. ........ 623/1.15 |
| 2004/0098100 A1 | * | 5/2004 | Williams et al. ........... 623/1.15 |

FOREIGN PATENT DOCUMENTS

| | | | | |
|---|---|---|---|---|
| EP | | 1 264 582 A2 | 12/2002 | |
| WO | | WO 9940874 A1 | * 8/1999 | ............. A61F/2/06 |

* cited by examiner

Primary Examiner—David H. Willse
Assistant Examiner—Javier G. Blanco
(74) Attorney, Agent, or Firm—Jones Day

(57) ABSTRACT

A percutaneously deliverable heart valve prosthesis and method of delivery, wherein the prosthesis is anchored to a valvular annulus of a patient and used to replace the patient's diseased valve. The prosthesis is supported by a rigid frame that is generally fixed, but capable of being modified between a first collapsed position and a second expanded position. In its first collapsed position, the prosthesis has sufficient flexibility and is of such a low profile that it allows for easy percutaneously delivery. Upon proper delivery, the prosthesis is anchored and modifiable to a generally permanent expanded position sufficiently rigid to resist the strong recoil force exerted by a distorted stenosed valve orifice displaced by the prosthesis.

54 Claims, 8 Drawing Sheets

PERCUTANEOUSLY DELIVERABLE HEART VALVE

FIELD OF THE INVENTION

The present invention relates to a prosthetic valve for implantation in a body channel, more particularly, to a percutaneously implantable prosthetic heart valve suitable for replacement of a defect or diseased human heart valve.

BACKGROUND OF THE INVENTION

Replacement heart valves or heart valve prostheses have been fabricated or manufactured for the last forty years. Such devices have been assembled from a variety of materials. Specifically the materials have been of biologic or artificial nature, generally leading to two distinct categories of the prostheses as biological or mechanical replacement heart valves.

The prosthetic heart valves are fabricated to replace the natural heart valves that, because of disease, congenital malformations, ageing or trauma have become dysfunctional and require repair to their functional elements or partial or complete replacement. Characteristics for a desirable prosthetic heart valve may include hemodynamic performance, thrombogenicity, durability and ease of surgical implantation.

Human heart valves under the conditions of normal physiological functions are passive devices that open under the pressure of blood flow on their leaflets. There are four valves in the heart that serves to direct the flow of blood through all chambers in a forward direction. In general, blood leaves the heart lower chambers in the direction to the rest of the body or to the lungs for required oxygenation, or blood enters the lower chambers from the upper chambers of the heart. Similarly, they close under the pressure exerted on the same leaflet elements when blood flow is retrograde, thus impeding return of blood flow to the chamber it has just left. This, under normal conditions, (that is, when the body is not under physical stresses and the heart is beating at the normal resting state of about 70 beats per minute) equates to the leaflets opening by separation from each other, thereby producing an opening or closing by apposing to each other approximately 38 million times per year. It can be surmised that under stress conditions this may be happening at higher rates, thus increasing the number of separations and appositions, as well as the forces of impact between the leaflets during the closing.

When disease conditions affect the structure of the materials of the components of the valve apparatus, the valve itself will decay, degenerate or disrupt and require repair or replacement to restore proper function necessary for the continuation of life.

The shape of the leaflet and surrounding elements of a valve or a valve apparatus is dependent on the function of the heart. In the case of the atrioventricular valves, otherwise known as mitral (in the left lower chamber of the heart) and tricuspid (in the right ventricle), the valve is part of a continuum that extends from the myocardium or muscular wall of the lower chambers, through the papillary muscles, to which is attached a confluence of tendinous rope-like elements known as chordae tendinae that themselves are attached to the edges of differently shaped leaflets which form the flow-allowing and flow-stopping or obstructing elements (leaflets). These leaflets continue and end at a ring-like structure usually known as annulus, that is part of the skeleton of the heart. It is this continuum which should be called an apparatus rather than just valve.

Thus, there is a tricuspid valve apparatus in the right ventricular chamber, and more importantly the mitral valve apparatus within the lower left heart chamber or left ventricle, the pumping function of which provides the systemic flow of blood through the aorta, to keep all tissues of the body supplied with oxygenated blood necessary for cellular function and life. Hence during the cardiac cycle, the valves function as part of a unit composed of multiple interrelated parts, including the ventricular and atria walls, the valve leaflets, the fibrous skeleton of the heart at the atrioventricular ring, and the subvalvular apparatus. The subvalvular apparatus includes the papillary muscle within the ventricle, and the chordae tendinae which connect the papillary muscle to the valve leaflets.

Aortic and pulmonary valves have been replaced with simple trileaflet chemically treated biological valves obtained from animals, or bileaflet mechanical valves without extreme deficiencies in valvular or cardiac function. This is not the case when mitral or tricuspid valves are replaced and the necessary involvement of chordae tendinae and muscular element of the chamber wall are not united to function in harmony with the valve leaflets. Those valves used in the aortic position cannot alone replace the mitral valve apparatus without anatomical and functional compromise.

Aortic stenosis is a disease of the aortic valve in the left ventricle of the heart. This aortic valvular orifice can become tightly stenosed, and therefore the blood cannot anymore be freely ejected from the left ventricle. In fact, only a reduced amount of blood can be ejected by the left ventricle which has to markedly increase the ventricular chamber pressure to pass the stenosed aortic orifice. In such aortic diseases, the patients can have syncope, chest pain, and mainly difficulty in breathing. The evolution of such a disease is disastrous when symptoms of cardiac failure appear and many patients die in the year following the first symptoms of the disease.

The only commonly available treatment is the replacement of the stenosed aortic valve by a prosthetic valve via open-heart surgery. If surgery is impossible to perform, i.e., if the patient is deemed inoperable or operable only at a too high surgical risk, an alternative possibility is to dilate the valve with a balloon catheter to enlarge the aortic orifice. Unfortunately, the result is sub-optimal with a high restenosis rate.

Aortic stenosis is a very common disease in people above seventy years old and occurs more and more frequently as the subject gets older. Until recently, the implantation of a valve prosthesis for the treatment of aortic stenosis is considered unrealistic to perform since it is deemed difficult to superpose another implantable valve on the distorted stenosed native valve without excising the latter.

Percutaneous Catheter-Based Delivery

Andersen et al. in U.S. Pat. No. 6,168,614, entire contents of which are incorporated herein by reference, discloses a heart valve prosthesis for implantation in the body by use of a catheter. The valve prosthesis is consisted of a support structure with a tissue valve connected to it, wherein the support structure is delivered in a collapsed shape through a blood vessel and secured to a desired valve location with the support structure in the expanded shape. However, the support structure is a generally fixed expandable-collapsible structure with little flexibility of modifying configuration at the collapsed shape for easy delivery percutaneously.

Andersen et al. in U.S. Pat. No. 5,840,081 and U.S. Pat. No. 5,411,552, entire contents of both of which are incorporated herein by reference, discloses a system for implanting a valve in a body channel comprising a radially collapsible and expandable stent with a valve mounted to it and a catheter for introducing and securing the valve in the body channel. The catheter generally comprises an expandable member about which the cylindrical stent may be positioned together with the valve, fastening means on the expandable member on which the stent may be mounted to the expandable member, and a channel extending through the catheter for injecting a fluid into the expandable member so as to expand the expandable member from a collapsed profile suitable for introduction into the body channel to an expanded profile in which the stent engages the inner wall of the body channel so as to secure the valve therein. Again, the cylindrical stent is a generally fixed expandable-collapsible structure with little flexibility of modifying configuration at the collapsed stage for easy delivery percutaneously. This type of design is inherently fragile, and such structures are not strong enough to be used in the case of aortic stenosis because of the strong recoil that will distort this weak structure and because they would not be able to resist the balloon inflation performed to position the implantable valve.

Letac et al. in U.S. Patent Application Ser. No. 2001/0007956 and No. 2001/0010017, entire contents of both are incorporated herein by reference, discloses a valve prosthesis for implantation in a body channel comprising a collapsible valvular structure and an expandable frame on which the valvular structure is mounted. However, the expandable frame is a generally fixed expandable-collapsible structure with little flexibility of modifying configuration or minimizing the profile at the collapsed stage for easy delivery percutaneously.

It is one aspect of the present invention to provide a percutaneously deliverable heart valve prosthesis comprising a tissue valve mounted on a support structure that has a plurality of collapsible crossbars with securing rings movably coupled any two adjacent crossbars at an appropriate location upon expanding the support structure of the implantable heart valve prosthesis.

Percutaneous Intercostal Delivery

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), or decalcification of valve and annulus tissue. Alternatively, the valve may be replaced, by excising the valve leaflets of the natural valve, and securing a replacement valve in the valve position, usually by suturing the replacement valve to the natural valve annulus.

A conventional procedure for approaching the left atrium is by intravascular catheterization from a femoral vein through the cardiac septal which separates the right atrium and the left atrium. In some aspects, this intravascular procedure is not only dangerous and tedious because of long tortuous route, but also limited use because of the catheter size suitable for insertion intravascularly.

Sterman et al. in U.S. Pat. No. 6,283,127, entire contents of which are incorporated herein by reference, discloses a device system and methods facilitating intervention within the heart or great vessels without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum. The device systems and methods are particularly well adapted for heart valve repair and replacement, facilitating visualization within the patient's thoracic cavity, repair or removal of the patient's natural valve, and, if necessary, attachment of a replacement valve in the natural valve position.

Of particular interest in the present application are techniques for the implantation of an atrioventricular valve that can be retracted or folded inside a delivery system or cannula for delivering through a less invasive intercostal penetration to the desired place, particularly in a left atrium. Thereafter the retracted valve with a support structure is released, expanded, crossbars secured by securing rings, separated from the delivery system, and secured to the desired anatomical place with a minimally invasive technique.

Most tissue valves applicable in the present invention are constructed by sewing the leaflets of pig aortic valves to a stent to hold the leaflets in proper position as a stented porcine valve. They may also be constructed by removing valve leaflets from the pericardial sac of cows or horses and sewing them to a stent as a stented pericardium valve. The stents may be rigid or slightly flexible and covered with cloth (usually a synthetic material sold under the trademark Dacron™ or Teflon™) and attached to a sewing ring for fixation to the patient's native tissue. In one embodiment, the porcine, bovine or equine tissue is chemically treated to alleviate any antigenicity.

The main advantage of tissue valves is that they do not cause blood clots to form as readily as do the mechanical valves, and therefore, the tissue valves do not typically require life-long systemic anticoagulation. Another advantage is that a tissue valve is so flexible that it can be shaped and configured for delivery percutaneously. However, the presence of the support structure consisted of a stent and sewing ring prevents the tissue valve from being anatomically accurate in comparison to a normal heart valve. It is one aspect of the present invention to provide a prosthetic heart valve with the expandable-collapsible support structure having flexibility of modifying configuration at the collapsed stage for easy delivery percutaneously.

Therefore, it would be desirable to provide a delivery system for delivering a prosthetic heart valve to a patient's heart configured to be releasably folded inside a lumen of the delivery system through a percutaneous intercostal penetration of a patient's chest or an opening at a carotid artery, jugular vein, subclavian vein, femoral vein and other blood vessel.

SUMMARY OF THE INVENTION

It is one object of the present invention to provide a foldable heart valve prosthesis to replace a diseased valve of a patient. The foldable heart valve prosthesis comprises a support structure with a diameter, wherein the support structure is foldable to a smaller diameter, the support structure comprising a plurality of close-loop crossbar frames, wherein each crossbar frame has a plurality of crossbars connected at an end of any two adjacent crossbars, and a flexible tissue heart valve with a plurality of valvular leaflets attached to the support structure. The prosthesis may further comprise a plurality of slidable ring connectors, wherein at least a slidable ring connector encircles a first crossbar from a first crossbar frame and a second crossbar from a second crossbar frame configured to couple the first and the second crossbars. In one aspect, the slidable ring connector is shrinkable to a smaller diameter after encircling the two crossbars.

It is another object of the present invention to fabricate a flexible tissue heart valve to be coupled with the support structure, wherein the tissue valve may be a porcine valve or a valve fabricated from pericardium tissue selected from a group consisting of equine, bovine, porcine, and ovine.

It is still another object of the present invention to provide a method for minimally invasively delivering a foldable heart valve prosthesis into a patient. The method comprises folding the support structure with the attached tissue heart valve inside a lumen of a delivery apparatus; delivering the delivery apparatus to a target valvular annulus of the patient; unfolding the support structure to deploy the foldable heart valve prosthesis in place; and coupling the crossbars by sliding the slidable ring connectors to an appropriate location of the crossbars. In one embodiment, the method may further comprise a shrinking step after the coupling step, wherein the shrinking step reduces a circumferential length of the slidable ring connector.

It is a preferred object of the present invention to provide a delivery system and methods for minimally invasively delivering a foldable heart valve prosthesis into anterior of a patient heart. In one embodiment, the delivery system has a differentially expandable balloon on the balloon catheter that is configured to expand the circularly folded valve into a deployed oval shape configuration, wherein the differentially expandable balloon comprises a longitudinal axis, a major traverse axis and a minor traverse axis, the major traverse axis being at least 10% longer than the minor traverse axis. Preferably, the major traverse axis is at least 50% longer than the minor traverse axis.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
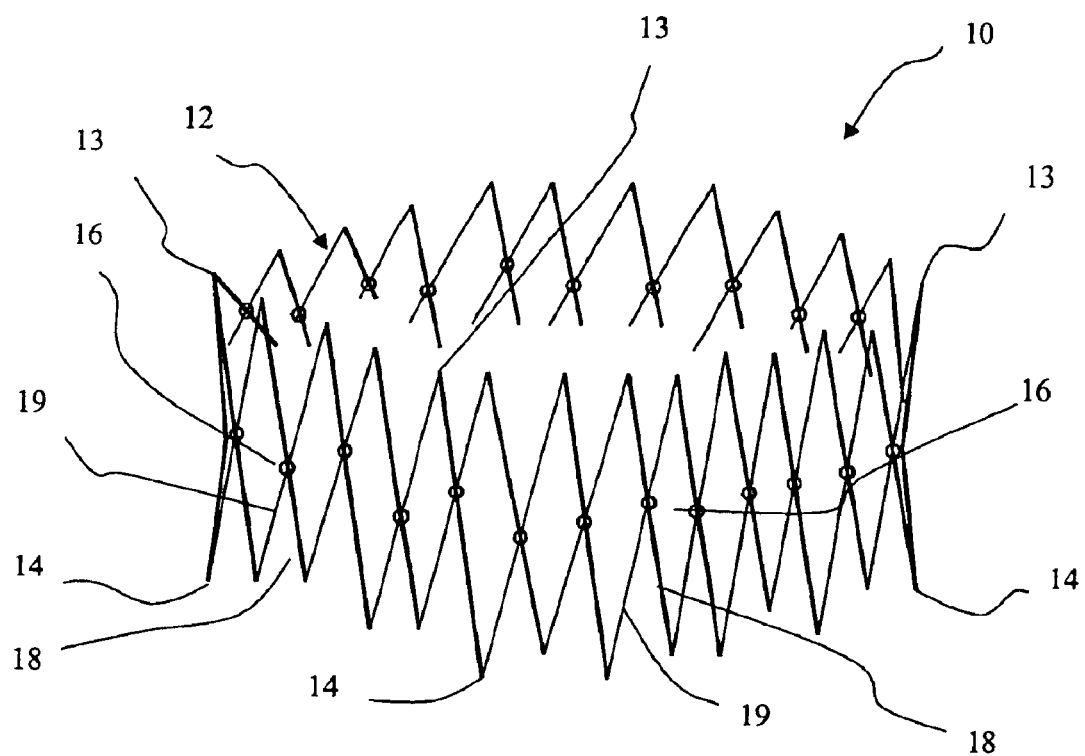
FIG. 1 is an expandable-collapsible heart valve prosthesis comprising a generally cylindrical support structure with slidable ring connectors at a fully expanded state in accordance with one embodiment of the present invention.

Referring to FIGS. 1 to 8, what is shown is an embodiment of a percutaneously deliverable heart valve prosthesis and delivery means thereof, including an illustrative cardiac valve. The same principles of percutaneously implantable valves could also apply to implantation of a venous valve, an esophagus valve, ureter valve, a biliary valve, and a valve in the intestines or in the lymphatic systems. While the description sets forth various embodiment specific details, it will be appreciated that the description is illustrative only and should not to be construed in any way as limiting the invention. Furthermore, various applications of the invention, and modifications thereto, which may occur to those who are skilled in the art, are also encompassed by the general concepts described below.

Andersen et al. in U.S. Pat. Nos. 6,168,614, 5,840,081 and 5,411,552 discloses a valve prosthesis for implantation in the body by use of a catheter comprising a stent made from an expandable cylinder-shaped thread structure comprising several spaced apices. The elastically collapsible valve is mounted on the stent at the commissural points of the valve and is secured to the projecting apices. The valve prosthesis can be compressed around the balloon of the balloon catheter and be inserted in the aorta. When the valve prosthesis is placed correctly, the balloon is inflated thereby expanding the stent and wedging it against the wall of the aorta. The balloon is provided with beads to ensure a steady fastening of the valve prosthesis on the balloon during insertion and expansion. However, Andersen et al. does not teach a stent coupled with slidable ring connectors configured for maintaining the stent structure at its minimal profile when the stent structure is collapsibly loaded into the balloon catheter.

Letac et al. in U.S. Patent Application Ser. No. 2001/0007956 and No. 2001/0010017, entire contents of both are incorporated herein by reference, discloses a valve prosthesis for implantation in a body channel comprising a collapsible valvular structure and an expandable frame on which the valvular structure is mounted. The valvular structure is composed of a valvular tissue compatible with the human body and blood, the valvular tissue being sufficiently supple and resistant to allow the valvular structure to be deformed from a closed state to an opened state. The valvular tissue forms a continuous surface and is provided with guiding means formed or incorporated within, the guiding means creating stiffened zones which induce the valvular structure to follow a patterned movement in its expansion to its opened state and in its turning back to its closed state. However, Letac et al. does not teach an expandable frame secured with slidable ring connectors configured for maintaining the frame structure at its minimal profile when the frame structure is collapsibly loaded into the delivery catheter.

The crossbars of the support frame as taught by Letac et al. are soldered together. Therefore, substantial force is needed to compressively fold the frame structure. When the folded frame structure is accidentally released from a constraint, it is quite difficult to reload the folded frame structure back into the lumen of the delivery apparatus.

Garrison et al. in U.S. Pat. No. 6,425,916, entire contents of which are incorporated herein by reference, discloses a valve implantation system comprising a valve displacer and a replacement valve. The valve displacer and the valve are in a collapsed condition during introduction and are expanded to deploy the valve displacer and the valve. However, Garrison et al. does not teach an expandable support structure secured with slidable ring connectors configured for maintaining the frame structure at its minimal profile when the support structure is collapsibly loaded into a delivery means.

FIG. 1 shows an expandable-collapsible heart valve prosthesis 10 comprising a generally cylindrical support structure 12 at a fully expanded or unfolded state in accordance with one embodiment of the present invention. In one aspect of the present invention, the support structure 12 may be made of a plurality of expandable metallic frames, each frame having crossbars 18, 19 configuration or other suitable configurations that are coupled by one or more of the slidable ring connectors 16. Each metallic frame forms a closed loop; that is, one end of the metallic frame is secured to the other end. The height of each of the crossbars 18, 19 is configured in a proper length sufficient to support a valvular structure or a tissue heart valve.

The cross-sectional diameter of the cylindrical support structure 12 is preferred to be about a few millimeters at a folded state to about 10 mm or larger at a fully unfolded state. The number and size of the crossbars 18, 19 are adapted to be sufficiently strong and rigid when the support structure is fully expanded in a target valvular orifice and coupled by the slidable ring connectors 16 to resist the strong recoil force exerted by the distorted stenosed valve orifice after unfolding the support structure 12. In one embodiment, upon being folded with little force, the diameter of the support structure is about 4 to 5 millimeters range, in view of its transcutaneous introduction. When positioned in the aortic orifice, the frame is able to expand under the force of an inflated balloon up to a size of 20 to 23 mm in diameter and locked in by the slidable ring connectors of the present invention. In another aspect of the present invention, the support structure along with its tissue heart valve is self-expandable or could be expanded by other means.

The expanded foldable heart valve prosthesis of the present invention is intended to replace a diseased valve of a patient. The valve prosthesis 10 may comprise a support structure 12 in a generally cylindrical or other appropriate configuration with a diameter, wherein the support structure 12 comprises a plurality of crossbar frames, the support structure being foldable to a smaller diameter. The valve prosthesis 10 may also comprise a flexible tissue valve with a plurality of valvular leaflets attached to the support structure 12. Finally, the valve prosthesis 10 comprises a plurality of slidable ring connectors to couple the crossbar frames. Each crossbar frame has an upper edge 13 and lower edge 14, wherein the edges 13, 14 may be configured to form a sharp edge or a round edge adapted for effectively supporting the tissue valve without undue stress or obstruction.

Figure 2:
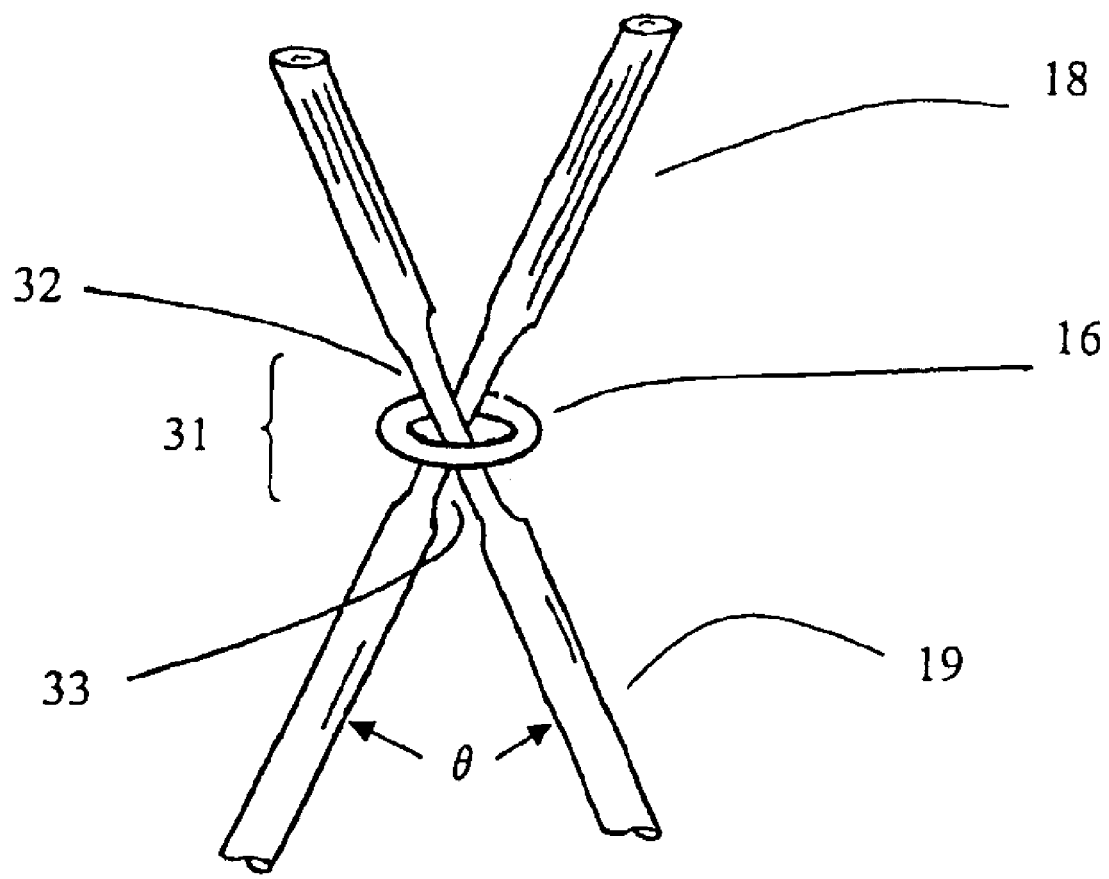
FIG. 2 is one embodiment of the crossbars with a slidable ring connector.

FIG. 2 shows one embodiment of the crossbars 18, 19 with a slidable ring connector 16. The crossbars 18, 19 have a trough or recess 33, 32, respectively at a medium region 31, wherein the medium region 31 may be located at a place away from the upper edge 13 or the lower edge 14. The slidable ring connector 16 is utilized to couple the two crossbars 18, 19 together to form the support structure 12 of the present invention. In one aspect, the ring connector 16 is made of an elastic material that can snugly compress against the crossbars 18, 19 at their recess zones 33, 32 or at other suitable zone. In another aspect, the slidable ring connector 16 is made of a coil spring material or circumferentially compressible material. In still another aspect, the slidable ring connector is made of a shape-memory material configured to shrinkably coupling the two adjacent crossbars snugly, wherein the shape-memory material is either a plastic shape-memory material or a Nitinol shape-memory material. The shape-transition temperature of the shape-memory material is preferably between about 39° C. to about 90° C. The shape-transition temperature is more preferably between about 40° C. to about 50° C., a temperature range compatible to human tissue. One method to effect the shape-memory material to reach its shape-transition temperature is to apply radiofrequency energy through an inserted conductive wire. Other means of raising the temperature to above the shape-transition temperature, such as warm saline flushing, is also applicable. The high frequency energy ablation or means for raising the temperature is well known to an ordinary artisan who is skilled in the art.

The medium region 31 where the recess portions of two crossbars meet with a slidable ring connector 16 may be configured to be near the upper edge 13. In this case, the circumference of the upper extremity of the support structure is smaller than the circumference of the lower extremity of the support structure because the ring connector holds any two crossbars together at near the upper edge 13. Similarly, the recess portions of the two crossbars along with a slidable ring connector 16 may be configured to be near the lower edge 14 so that the circumference of the lower extremity of the support structure is smaller than the circumference of the upper extremity of the support structure The angle θ formed between the two crossbars 18, 19 dictates the overall circumference of the support structure. The wider the angle θ, the larger the overall circumference. It is also within the scope of the present invention that the first angle θ formed between the first two crossbars may be different from the second angle θ formed between the second two crossbars. The slidable ring connector 16 is generally configured and sized to show minimal ring circumference after being coupled to the crossbars and shrunk, wherein the angle θ formed between the crossbars 18, 19 after being coupled is generally at least 15 degrees.

The recesses 33, 32 of the crossbars 18, 19 may face to each other and configure to have a minimal profile while yield an adequate strength for the support structure in its intended purposes for supporting the prosthesis. In one embodiment, the surface of the recess is flat so as to match both recess surfaces. In another embodiment, the surface of the recess is rough to enhance coupling force when compressed by the shrunk slidable ring connector 16. In still another embodiment, the surface of one recess is lined or curved to match the surface of the other matching recess.

The crossbars 18, 19 and the ring connector 16 are made of biocompatible material, wherein the slidable ring connector is sized and configured to secure the crossbars together as a part of the support structure 12 enabling effective mounting and/or functioning of the valvular structure. The support structure may have protrusions, barbs, needles, or other anchoring mechanism for engaging the valve prosthesis to the valvular annulus of a patient.

Figure 3:
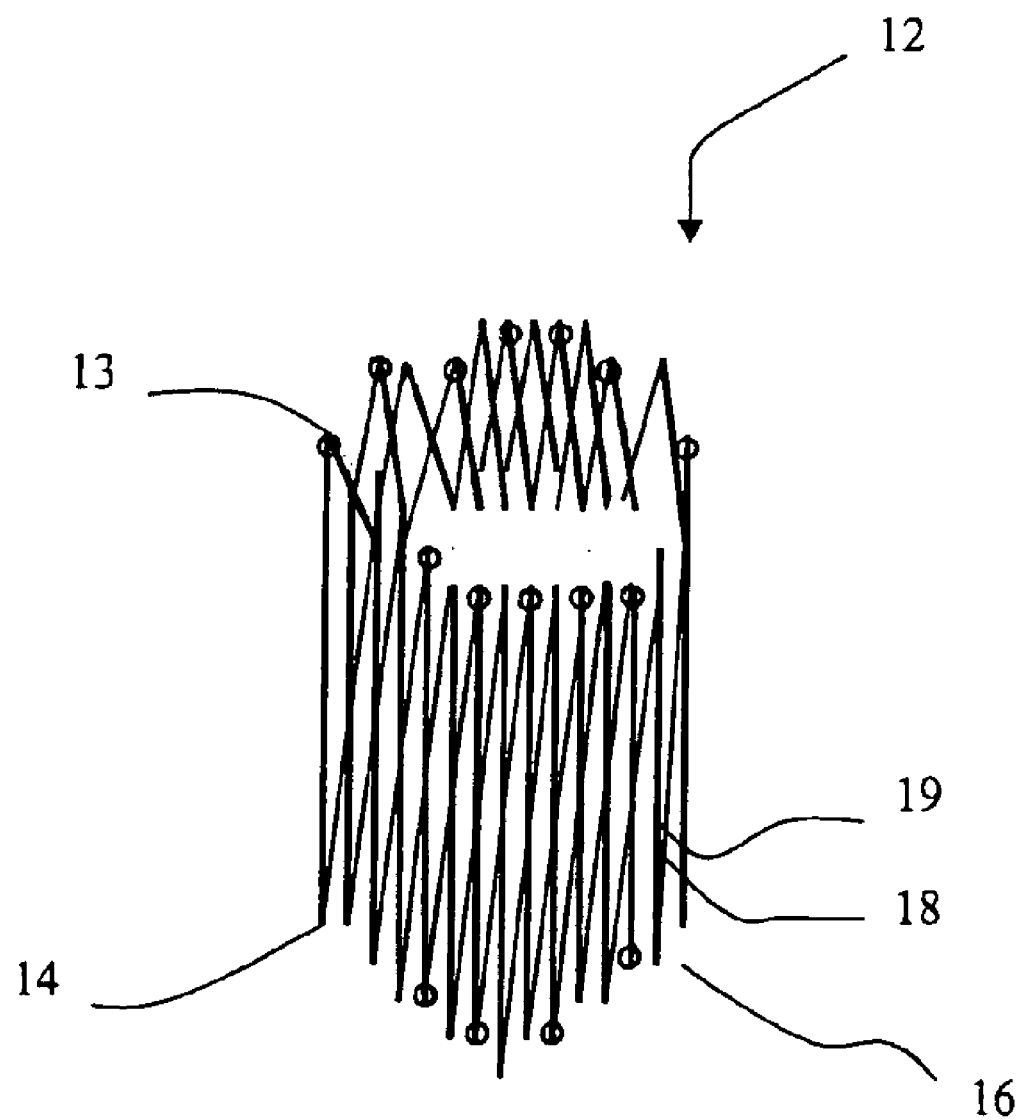
FIG. 3 is an expandable-collapsible heart valve prosthesis of FIG. 1 comprising a generally cylindrical support structure with slidable ring connectors at a collapsed state.

FIG. 3 shows an expandable-collapsible heart valve prosthesis of FIG. 1 comprising a generally cylindrical support structure 12 at a collapsed state. In one embodiment, at least one of the slidable ring connectors 16 is slid to near the upper edge 13. In another embodiment, at least one of the slidable ring connectors 16 is slid to near the lower edge 14 of the support structure 12. While sliding most of the ring connectors 16 to an upper edge 13 or lower edge 14, the overall profile at about that edge is relatively small. In some aspect of the present invention, the ring connector is loosely overlaid with the crossbars 18, 19 during the unfolded state. In this case, it requires little force to compress the foldable heart valve prosthesis to be inserted inside a delivery apparatus during the device delivery phase.

Figure 4:
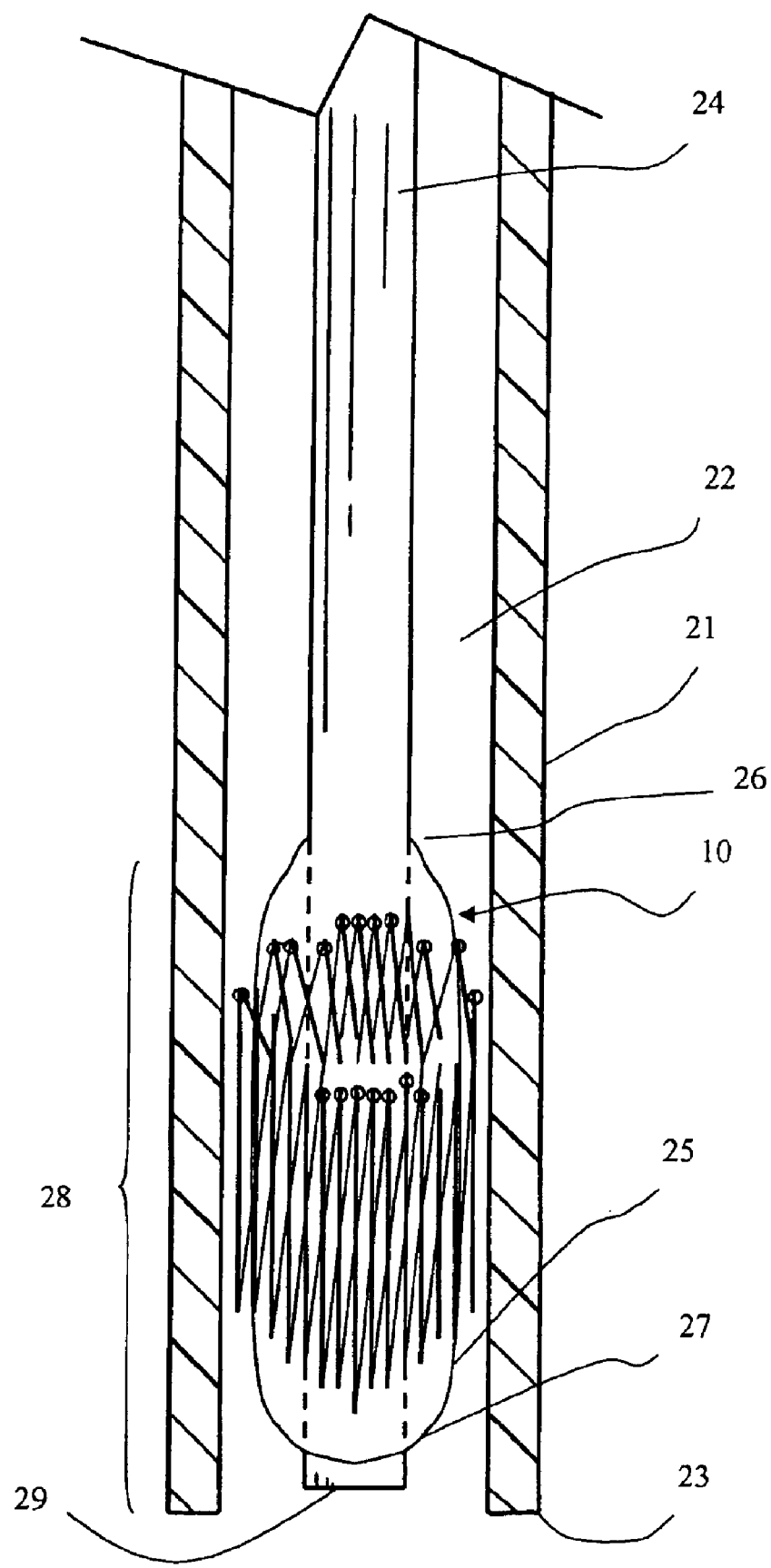
FIG. 4 is a cross-sectional view of a delivery apparatus enclosing an expandable-collapsible heart valve prosthesis comprising a generally cylindrical support structure at a collapsed state.

FIG. 4 shows a foldable heart valve prosthesis 10 of FIG. 1 comprising a generally cylindrical support structure at a folded state suitable for percutaneous delivery by a delivery apparatus 21, such as a catheter, a cannula or an endoscopic instrument. The crossbars 18, 19 according to the principles of the present invention are configured and sized to be flexible longitudinally for easy delivery passing the tortuous natural conduits or openings. It is particularly practical to loosen the crossbar coupling by sliding the ring connector 16 close to one edge 13, 14 of the crossbar frames. However, the crossbars 18, 19 of the crossbar frames have adequate hoop strength (that is, the strength in an outwardly radial direction of the circular support structure) to expand the valvular annulus and resist the strong recoil force exerted by the distorted stenosed valve orifice after snugly coupling any two adjacent crossbars.

FIG. 4 shows a cross-sectional view of a delivery apparatus enclosing a foldable heart valve prosthesis comprising a generally cylindrical support structure at a folded or collapsed state. In one embodiment as show in FIG. 4, the delivery apparatus may comprise a catheter 21, wherein the catheter passes through an opening of the body, such as an incision at a carotid artery, a jugular vein, a subclavian vein, or any body vessel. In another embodiment, the delivery apparatus may comprise a cannula, the cannula passing through a percutaneous intercostal penetration.

The foldable heart valve prosthesis of the present invention comprises a support structure and a flexible tissue heart valve with a plurality of valvular leaflets attached to the support structure. The flexible tissue heart valve may be a porcine valve or a valve fabricated from pericardium tissue selected from a group consisting of equine, bovine, porcine, and ovine. In one aspect of the present invention, the porcine valve is procured from a genetically modified porcine, wherein the procured porcine valve is with little rejection when transplanted. The flexible tissue heart valve may further be chemically treated to reduce antigenicity of the tissue material, wherein the chemical is selected from a group consisting of glutaraldehyde, formaldehyde, dialdehyde starch, and polyepoxy compounds. The flexible tissue heart valve is generally mounted on the support structure at the commissural points of the valve and is secured to the crossbar frames. In a further embodiment, the flexible tissue heart valve is fastened along a substantial portion of an expandable crossbar frame, by sewing, stitching, molding or gluing so as to fabricate the expandable-collapsible prosthesis to sufficiently prevent any regurgitation of the body fluid between the support structure and the valvular structure of the tissue heart valve.

It is some aspect of the present invention to provide a method for minimally invasively delivering a foldable heart valve prosthesis 10 into a patient. The method may comprise the steps of: (a) folding the support structure with the attached flexible tissue heart valve inside a lumen of a delivery apparatus; (b) delivering the delivery apparatus to a target valvular annulus of the patient; (c) unfolding the support structure to deploy the folded heart valve prosthesis in place; and (d) coupling the crossbars by sliding the slidable ring connector to an appropriate location of the crossbars. The method may further comprise a step of shrinking the ring to tightly coupling the crossbars with the ring connector.

In one embodiment, the method may further comprise a step of removing at least a portion of a patient's heart valve by means of a cutting tool introduced through the percutaneous intercostal penetration and through an internal penetration on a cardiac wall before the folding step. In some aspect of the present invention, the cutting tool may be made of an electrically conductive metal and radiofrequency energy is provided to the cutting tool for enhanced valve removal. The high frequency energy ablation is well known to an ordinary artisan who is skilled in the art.

The method may further comprise a step of fastening the unfolded heart valve within the valvular annulus by means of an instrument introduced through the percutaneous intercostal penetration and through an internal penetration on a cardiac wall after the unfolding step. The process of removing at least a portion of a patient's heart valve by means of a cutting tool and the process of fastening the unfolded heart valve within the valvular annulus by means of an instrument introduced through the percutaneous intercostal penetration and through an internal penetration on a cardiac wall is well know to one ordinary artisan who is skilled in the art.

The delivery apparatus 21 comprises a distal section 28, a distal end 23 and a lumen 22, wherein a device deployment mechanism (not shown) is located within the lumen 22 of the delivery apparatus 21. At least one slidable ring connector is slid to an end or close to an end of a crossbar when the heart valve prosthesis is being folded. The foldable heart valve prosthesis 10 in its folded state stays inside the lumen 22 of the delivery apparatus 21 as shown in FIG. 4 during the delivery phase through an intercostal penetration or through an opening of the blood vessel. In one embodiment, the folded heart valve prosthesis 10 is wrapped outside of a balloon 25 of an inner member 24, wherein the balloon 25 has a distal end 27 and a proximal end 26 securely attached onto the inner member 24. The inner member 24 has a distal end 29 and a fluid communication system for inflating the balloon 25. The balloon may be selected from a group consisting of compliant material, non-compliant material, and/or semi compliant material.

Figure 5:
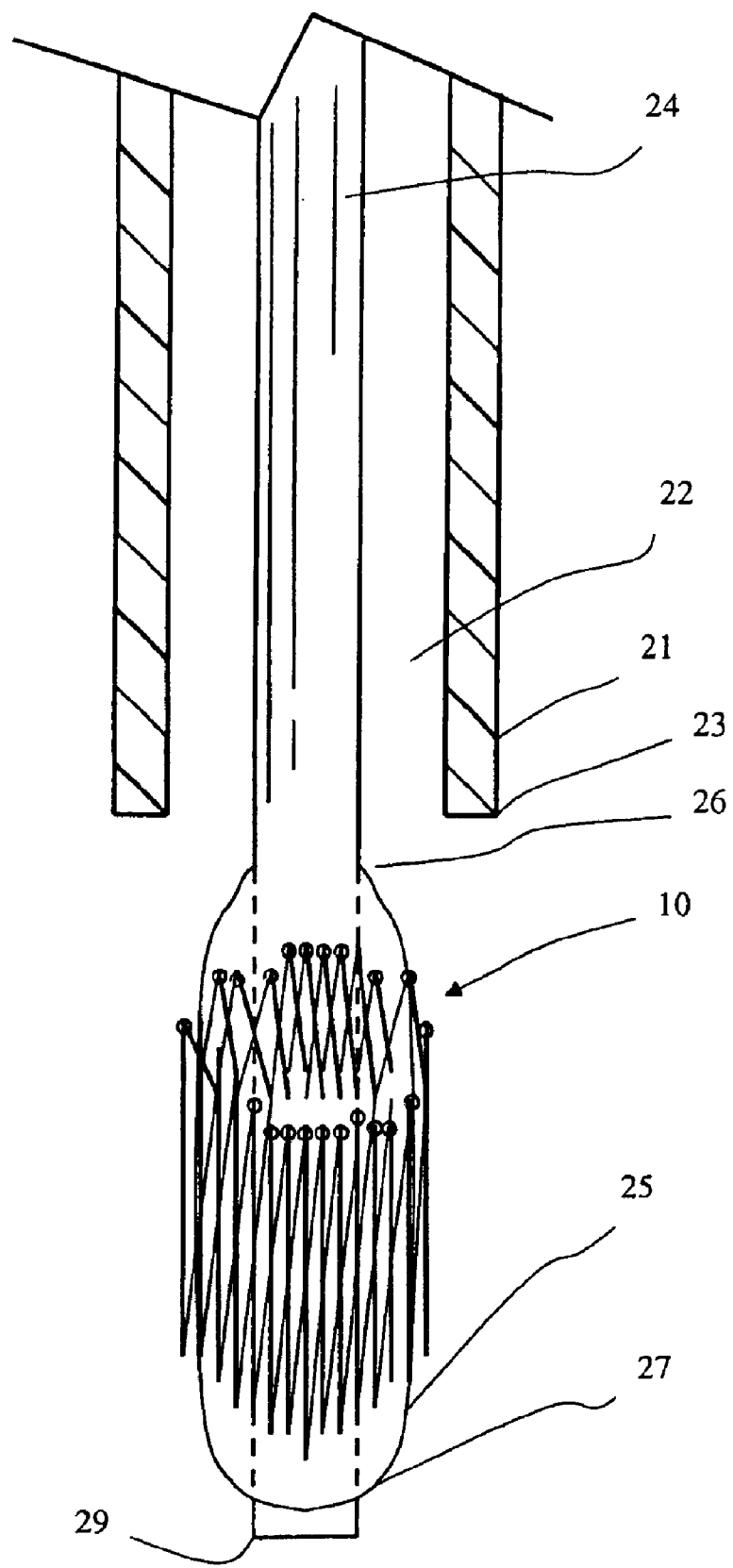
FIG. 5 is a first step for delivering an expandable-collapsible heart valve prosthesis at a folded state out of a delivery apparatus.

Once the distal section of the delivery apparatus arrives at an appropriate location adjacent the valvular annulus of the diseased heart valve, the folded heart valve prosthesis 10 is pushed out of the distal end 23 of the delivery apparatus 21 (shown in FIG. 5). The delivery apparatus may further comprise an expanding element, for example a balloon 25 or an expandable basket, to unfold and expand the cylindrical support structure 12. In another aspect, the support structure is self-expandable.

Figure 6:
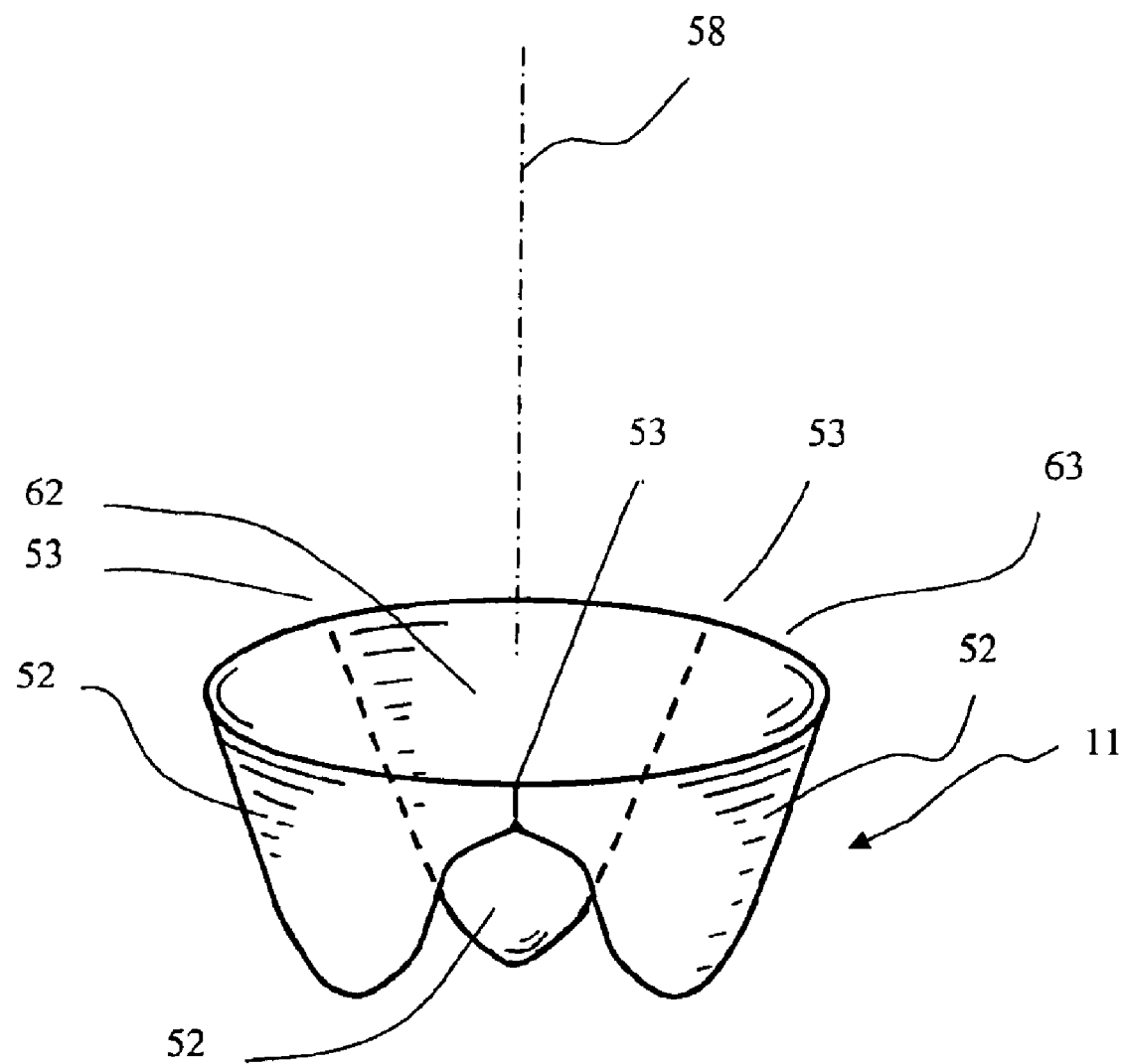
FIG. 6 is a perspective view of a tissue valve component of an expandable-collapsible aortic heart valve prosthesis comprising a plurality of tissue leaflets at a fully unfolded state.

FIG. 6 shows a perspective view of a tissue valve component 11 of an expandable-collapsible aortic heart valve prosthesis comprising a plurality of tissue leaflets 52 at a fully unfolded state. At a leaflet-open state, the opening 62 of the heart valve prosthesis allows blood to pass through. The flexible annular ring 63 as a part of the flexible tissue heart valve 11 has a central axial line 58 and commissural points 53. The flexible tissue heart valve is generally mounted onto the support structure at the commissural points of the valve and is secured to the crossbar frames of the support structure.

Figure 7:
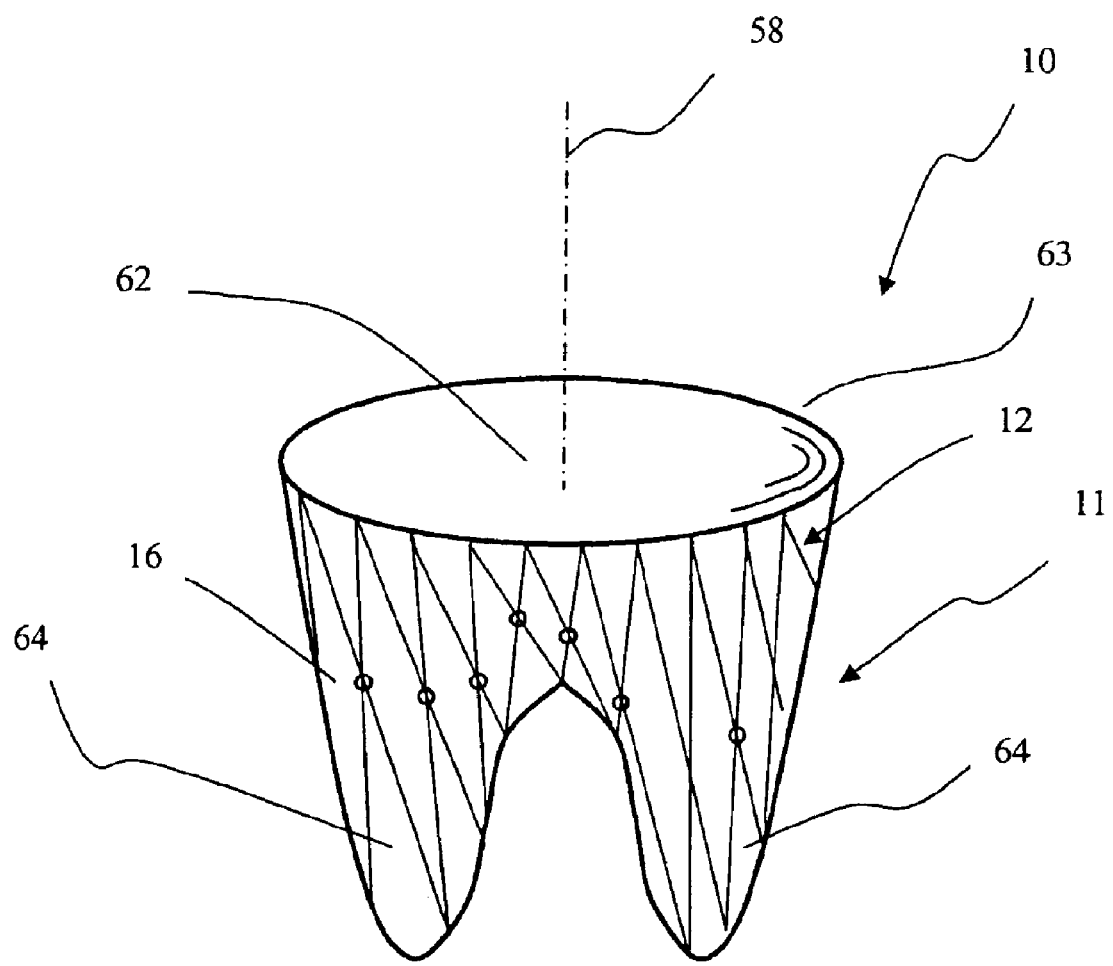
FIG. 7 is a perspective view of an expandable-collapsible atrioventricular heart valve prosthesis at a fully unfolded state.

FIG. 7 shows a perspective view of an expandable-collapsible atrioventricular heart valve prosthesis 10 comprising a support structure 12 and a flexible tissue heart valve 11 with a plurality of tissue leaflets 64 at a fully unfolded state. At a leaflet-open state, the opening 62 allows blood to pass through. The flexible annular ring 63 as a part of the flexible tissue heart valve 11 has a central axial line 58 and the flexible tissue heart valve 11 is generally mounted and secured onto the support structure 12. The slidable ring connector 16 is deployed and utilized to enable unfolding the cylindrical crossbar frames against the strong recoil force exerted by the distorted stenosed valve orifice. In one aspect, at least a slidable ring connector encircles a first crossbar from a first crossbar frame and a second crossbar from a second crossbar frame configured to couple the first and the second crossbars. In another aspect, some pairs of the crossbars do not have a slidable ring connector to maintain the proper rigidity of the support structure 12. In still another aspect, some pairs of the crossbars have a plurality of slidable ring connectors spaced apart to maintain the proper rigidity of the support structure 12.

Figure 8:
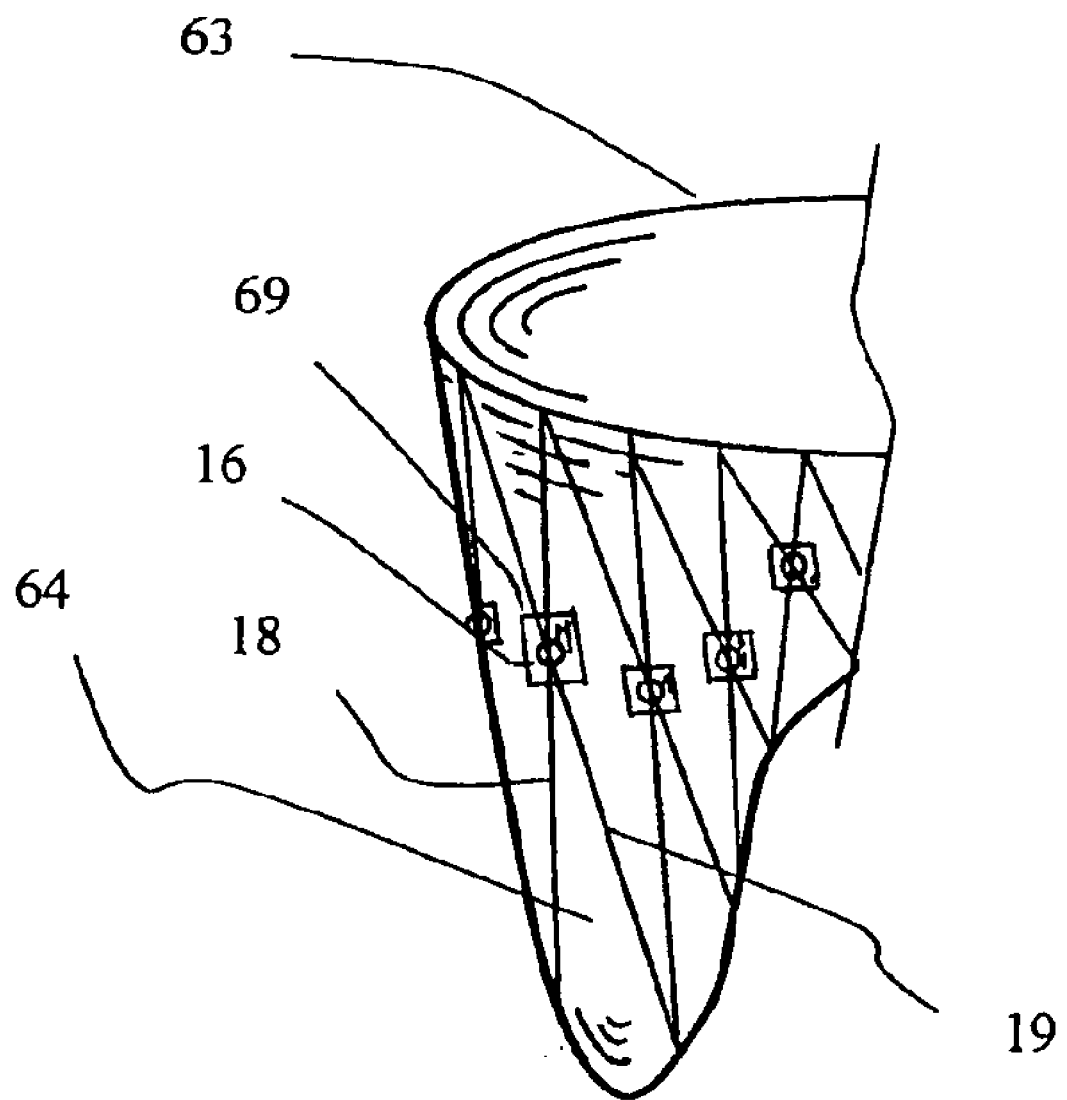
FIG. 8 is a partial perspective view of an expandable-collapsible atrioventricular heart valve prosthesis at a fully unfolded state.

FIG. 8 shows a partial perspective view of an expandable-collapsible atrioventricular heart valve prosthesis at a fully expanded state. Myers et al. in U.S. Patent Application publication 2002/0052651, entire contents of which are incorporated herein by reference, discloses a tubular prosthetic semilunar or atrioventricular heart valve by adding substantially rectangular commissural mounting pads at the distal end. The commissural mounting pad is generally used for stitching or suturing purposes. It is one aspect of the present invention to incorporate a mounting pad 69 at between the slidable ring connector 16 and the tissue of the flexible tissue valve for anchoring the slidable ring connector once the heart valve prosthesis is deployed at a target location of the patient.

It is one object of the present invention to provide an expandable-collapsible heart valve prosthesis to replace a diseased valve of a patient. The diseased heart valve to be replaced may be selected from a group consisting of an aortic valve, a pulmonary valve, and an atrioventricular valve of mitral or tricuspid valves. The foldable heart valve prosthesis is usually folded to be within a delivery catheter of about less than 24 French, corresponding to about 8 mm in diameter. The heart valve prosthesis may comprise (a) a support structure with a diameter, wherein the support structure is foldable to a smaller diameter, the support structure comprising a plurality of crossbar frames, wherein each crossbar frame has a plurality of crossbars; (b) a flexible tissue heart valve with a plurality of valvular leaflets attached to the support structure; and (c) a plurality of slidable ring connectors, wherein at least a slidable ring connector encircles a first crossbar from a first crossbar frame and a second crossbar from a second crossbar frame configured to couple the first and the second crossbars.

The delivery apparatus 21 may be made from plastic material, metal or composite material. In one embodiment, the delivery apparatus may be made of the material selected from the group consisting of polyethylene, polypropylene, polycarbonate, nylon, polytetrafluoroethylene, polyurethane, stainless steel, Nitinol, titanium, polyimide, polyester, and the like.

In operation, a delivery apparatus 21 of the present invention may be deployed through an intercostal penetration. The delivery apparatus may be introduced through a cannula or trocar positioned in one of percutaneous intercostal penetrations, the cannula or trocar having a proximal end disposed outside of the patient and a distal end disposed within the chest. The delivery means through a percutaneous intercostal penetration is well known to one who is skilled in the art, such as that proposed and taught by Sterman et al. in U.S. Pat. No. 6,283,127, entire contents of which are incorporated herein by reference, disclosing a device system and methods facilitating intervention within the heart without the need for a median sternotomy or other form of gross thoracotomy, substantially reducing trauma, risk of complication, recovery time, and pain for the patient.

It is one object of the present invention to provide a method for minimally invasively delivering a foldable heart valve into a patient. The method comprises: folding the valve within a lumen of delivery means for delivering the valve to a target valvular annulus of the patient; unfolding the valve in place by a balloon catheter, wherein a differentially expandable balloon of the balloon catheter is configured to expand the circularly folded valve into an oval unfolded valve, and coupling the crossbars by sliding the slidable ring connector to an appropriate location of the crossbars and locking in, wherein the foldable heart valve comprises a support structure having a plurality of crossbars and a plurality of shrinkable slidable ring connectors.

In one aspect of the present invention, the differentially expandable balloon comprises a longitudinal axis, a major traverse axis and a minor traverse axis, the major traverse axis being at least 10% longer than the minor traverse axis. Preferably, the major traverse axis is at least 50% longer than the minor traverse axis. In another aspect of the present invention, the differentially expandable balloon is delivered through a percutaneous intercostal penetration of the patient.

The method may further comprise a shrinking step after the coupling step, wherein the shrinking step reduces a circumferential length of the slidable ring connector. In one aspect, the shrinking step is carried out by raising a temperature of the ring connector above a shape-transition temperature of a shape-memory material, the slidable ring connector being made of the shape-memory material, wherein the shape-memory material is either a plastic shape-memory material or a Nitinol shape-memory material. The shape-transition temperature of the shape-memory material is preferably between about 39° C. to about 90° C., more preferably between about 40° C. to about 50° C.

From the foregoing description, it should now be appreciated that a percutaneously deliverable heart valve prosthesis suitable for replacement of a diseased human heart valve and delivery means thereof have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A foldable heart valve prosthesis to replace a diseased valve of a patient comprising:
   a support structure with a diameter, wherein the support structure is foldable to a smaller diameter, the support structure comprising a plurality of crossbar frames, wherein each crossbar frame has a plurality of crossbars connected at an end of each crossbar;
   a flexible tissue heart valve with a plurality of valvular leaflets attached to said support structure; and
   a plurality of slidable ring connectors, wherein at least one slidable ring connector encircles a first crossbar from a first crossbar frame and a second crossbar from a second crossbar frame, said at least one slidable ring connector configured to coupling the first and the second crossbars.

2. The foldable heart valve prosthesis of claim 1, wherein the flexible tissue heart valve is a porcine valve.

3. The foldable heart valve prosthesis of claim 1, wherein the flexible tissue heart valve is made of pericardium tissue selected from a group consisting of equine, bovine, porcine, and ovine.

4. The foldable heart valve prosthesis of claim 2 or claim 3, wherein the flexible tissue heart valve is chemically treated to reduce antigenicity of said tissue material.

5. The foldable heart valve prosthesis of claim 4, wherein the flexible tissue heart valve is chemically treated with a chemical selected from a group consisting of glutaraldehyde, formaldehyde, dialdehyde starch, and polyepoxy compounds.

6. The foldable heart valve prosthesis of claim 1, wherein at least one slidable ring connector is slid to adjacent an end of the first crossbar when said heart valve prosthesis is folded.

7. The foldable heart valve prosthesis of claim 1, wherein the first crossbar of the first crossbar frame has a recess configured for coupling the second crossbar of the second crossbar frame.

8. The foldable heart valve prosthesis of claim 7, wherein the second crossbar comprises a recess, the recess of the first crossbar facing the recess of the second crossbar.

9. The foldable heart valve prosthesis of claim 7, wherein the recess of the first crossbar is located close to an end of the first crossbar.

10. The foldable heart valve prosthesis of claim 1, wherein the slidable ring connector is made of an elastic material.

11. The foldable heart valve prosthesis of claim 1, wherein the slidable ring connector is made of a coil spring material.

12. The foldable heart valve prosthesis of claim 1, wherein the at least one slidable ring connector is made of a shape-memory material configured to shrinkably coupling the first crossbar and the second crossbar snugly.

13. The foldable heart valve prosthesis of claim 12, wherein the shape-memory material is either a plastic shape-memory material or a Nitinol shape-memory material.

14. The foldable heart valve prosthesis of claim 13, wherein a shape-transition temperature of the shape-memory material is between about 40° C. to about 50° C.

15. The foldable heart valve prosthesis of claim 1, wherein the flexible tissue heart valve is an aortic valve.

16. The foldable heart valve prosthesis of claim 1, wherein the flexible tissue heart valve is a pulmonary valve.

17. The foldable heart valve prosthesis of claim 1, wherein the flexible tissue heart valve is an atrioventricular valve.

18. The foldable heart valve prosthesis of claim 1, wherein the flexible tissue heart valve is generally mounted on the support structure at commissural points of said flexible tissue heart valve and is secured to the crossbar frames.

19. The foldable heart valve prosthesis of claim 1, wherein the support structure is made of a material selected from a group consisting of polyethylene, polypropylene, polycarbonate, nylon, polytetrafluoroethylene, polyurethane, stainless steel, Nitinol, titanium, polyimide, polyester, shape-memory material, and mixture thereof.

20. The foldable heart valve prosthesis of claim 1, wherein the slidable ring connector is configured and sized to show minimal circumference after being coupled to the crossbars.

21. The foldable heart valve prosthesis of claim 20, wherein an angle of the coupled crossbars after being coupled with said slidable ring connector is at least 15 degrees.

22. The foldable heart valve prosthesis of claim 1, wherein the support structure is self-expandable.

23. A method for minimally invasively delivering a foldable heart valve prosthesis into a patient, the foldable heart valve prosthesis comprising a support structure with a diameter, wherein the support structure is foldable to a smaller diameter, the support structure comprising a plurality of crossbar frames, wherein each crossbar frame has a plurality of crossbars; a flexible tissue heart valve with a plurality of valvular leaflets attached to said support structure; and a plurality of slidable ring connectors, wherein at least one slidable ring connector encircles a first crossbar from a first crossbar frame and a second crossbar from a second crossbar frame, said at least one slidable ring connector configured to coupling the first and the second crossbars; said method comprising:
folding said support structure with the attached flexible tissue heart valve inside a lumen of a delivery apparatus;
delivering said delivery apparatus to a target valvular annulus of the patient;
unfolding said support structure to deploy said foldable heart valve prosthesis in place; and
coupling the first and second crossbars by sliding the at least one slidable ring connector to an appropriate location of the first and second crossbars.

24. The method of claim 23, wherein the delivery apparatus comprises a catheter.

25. The method of claim 24, wherein the delivery step is carried out with said catheter through an opening selected from a group consisting of a carotid artery, a jugular vein, a subclavian vein, and a body vessel.

26. The method of claim 24, wherein the catheter is made of a material selected from a group consisting of polyethylene, polypropylene, polycarbonate, nylon, polytetrafluoroethylene, polyurethane, stainless steel, Nitinol, titanium, polyimide, and polyester.

27. The method of claim 23, wherein the unfolding step is carried out by a support structure that is self-expandable.

28. The method of claim 23, wherein the delivery apparatus comprises a cannula.

29. The method of claim 28, wherein the delivery step is carried out with said cannula through a percutaneous intercostal penetration.

30. The method of claim 29 further comprising a step of removing at least a portion of a patient's heart valve by means of a cutting tool introduced through the percutaneous intercostal penetration and through an internal penetration on a cardiac wall before the unfolding step.

31. The method of claim 30, wherein the step of removing is carried out by providing radiofrequency energy to the cutting tool.

32. The method of claim 29 further comprising a step of fastening the unfolded heart valve within the valvular annulus by means of an instrument introduced through the percutaneous intercostal penetration and through an internal penetration on a cardiac wall after the unfolding step.

33. The method of claim 23, wherein the folding step is carried out after a step of sliding at least one of the slidable ring connectors to adjacent an end of the first crossbar.

34. The method of claim 23 further comprising a shrinking step after the coupling step, wherein the shrinking step reduces a circumferential length of the slidable ring connector.

35. The method of claim 34, wherein the shrinking step is carried out by raising a temperature of the at least one slidable ring connector above a shape-transition temperature of a shape-memory material, said slidable ring connector being made of said shape-memory material.

36. The method of claim 35, wherein the shape-memory material is either a plastic shape-memory material or a Nitinol shape-memory material.

37. The method of claim 35, wherein the shape-transition temperature of the shape-memory material is between about 40° C. to about 50° C.

38. The method of claim 23, wherein the flexible tissue heart valve is an aortic valve.

39. The method of claim 23, wherein the flexible tissue heart valve is a pulmonary valve.

40. The method of claim 23, wherein the flexible tissue heart valve is an atrioventricular valve.

41. The method of claim 23, wherein the flexible tissue heart valve is a porcine valve.

42. The method of claim 23, wherein the flexible tissue heart valve is made of pericardium tissue selected from a group consisting of equine, bovine, porcine, and ovine.

43. The method of claim 41 or 42, wherein the flexible tissue heart valve is chemically treated to reduce antigenicity of said tissue material.

44. The method of claim 43, wherein the flexible tissue heart valve is chemically treated with a chemical selected from a group consisting of glutaraldehyde, formaldehyde, dialdehyde starch, and polyepoxy compounds.

45. The method of claim 23, wherein the unfolding step is carried out by an inflatable balloon on a catheter.

46. The method of claim 45, wherein the balloon is selected from a group consisting of compliant material, non-compliant material, and semi compliant material.

47. A method for minimally invasively delivering a foldable heart valve into a patient, the foldable heart valve comprising a support structure having a plurality of crossbars and a plurality of slidable ring connectors;

said method comprising:

folding said valve within a lumen of a delivery means for delivering said valve to a target valvular annulus of the patient;

unfolding said valve in place by a balloon catheter, wherein a differentially expandable balloon of the balloon catheter is configured to expand the folded heart valve into an oval unfolded valve; and coupling the plurality of crossbars by sliding at least one of the plurality of slidable ring connectors to an appropriate location of the plurality of crossbars.

48. The method of claim 47, wherein said differentially expandable balloon comprises a longitudinal axis, a major traverse axis and a minor traverse axis, the major traverse axis being at least 10% longer than the minor traverse axis.

49. The method of claim 47, wherein said differentially expandable balloon is delivered through a percutaneous intercostal penetration of the patient.

50. The method of claim 49, wherein said differentially expandable balloon is delivered through an opening selected from a group consisting of a carotid artery, a jugular vein, a subclavian vein, and a body vessel.

51. The method of claim 47 further comprising a shrinking step after the coupling step, wherein the shrinking step reduces a circumferential length of the plurality of slidable ring connectors.

52. The method of claim 51, wherein the shrinking step is carried out by raising a temperature of the plurality of slidable ring connectors above a shape-transition temperature of a shape-memory material, said plurality of slidable ring connectors being made of said shape-memory material.

53. The method of claim 52, wherein the shape-memory material is either a plastic shape-memory material or a Nitinol shape-memory material.

54. The method of claim 52, wherein the shape-transition temperature of the shape-memory material is between about 40° C. to about 50° C.

* * * * *